(12) United States Patent
Bruns et al.

(10) Patent No.: US 12,115,371 B2
(45) Date of Patent: Oct. 15, 2024

(54) SYSTEM AND METHOD FOR REAL-TIME COCHLEAR IMPLANT LOCALIZATION

(71) Applicant: Vanderbilt University, Nashville, TN (US)

(72) Inventors: Trevor L. Bruns, Nashville, TN (US); Robert J. Webster, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 452 days.

(21) Appl. No.: 17/604,125

(22) PCT Filed: Apr. 17, 2020

(86) PCT No.: PCT/US2020/028835
§ 371 (c)(1),
(2) Date: Oct. 15, 2021

(87) PCT Pub. No.: WO2020/215000
PCT Pub. Date: Oct. 22, 2020

(65) Prior Publication Data
US 2022/0193412 A1 Jun. 23, 2022

Related U.S. Application Data

(60) Provisional application No. 62/835,912, filed on Apr. 18, 2019.

(51) Int. Cl.
*A61N 1/36* (2006.01)
*A61N 1/05* (2006.01)

(52) U.S. Cl.
CPC ....... *A61N 1/36039* (2017.08); *A61N 1/0541* (2013.01)

(58) Field of Classification Search
CPC .......................... A61N 1/36039; A61N 1/0541
See application file for complete search history.

(56) References Cited

U.S. PATENT DOCUMENTS

| 7,194,314 | B1 | 3/2007 | Richter |
| 2013/0079844 | A1 | 3/2013 | Conn |
| 2018/0043161 | A1 | 2/2018 | Laudanski |
| 2018/0280687 | A1 | 10/2018 | Carter |
| 2018/0296828 | A1 | 10/2018 | Bradley |

OTHER PUBLICATIONS

International Search Report and Written Opinion in International Application No. PCT/US2020/28835, mailed Jul. 23, 2020 (14 pages).

*Primary Examiner* — Joseph M Dietrich
(74) *Attorney, Agent, or Firm* — Nixon Peabody LLP

(57) ABSTRACT

A system and method for determining the location of an implant such as a cochlear implant relative to a structure of interest such as a tissue wall. The implant has an electrode array including a first electrode and a second electrode. The electrode array is insertable into an electrically-conductive volume relative to the inner wall of the scala tympani of the cochlea. A pulse generator generates a biphasic, constant-current pulse on the first and second electrodes. A controller measures the differential voltage across the pair of electrodes during the current pulse. The controller determines the proximity between the inner wall and the segment of the electrode array between the first and second electrodes based on the differential voltage between the first and second electrodes.

20 Claims, 8 Drawing Sheets

SYSTEM AND METHOD FOR REAL-TIME COCHLEAR IMPLANT LOCALIZATION

PRIORITY CLAIM

This application is a U.S. National Stage Entry of International Application No. PCT/US2020/028835, filed on Apr. 17, 2020, which claims priority to U.S. Provisional Application No. 62/835,912, titled "Electrical Impedance Method For Cochlear Implant Localization" and filed on Apr. 18, 2019, the contents of which are incorporated herein by reference in its entirety.

FIELD OF THE TECHNOLOGY

The present technology relates to determining the location of implants, and specifically to using a real-time electrical impedance process for determining cochlear implant location.

BACKGROUND

A cochlear implant is a neuroprosthetic device capable of restoring hearing to those with profound sensorineural hearing loss. A typical cochlear implant consists of two main components: the external sound processor worn behind the ear; and the internal receiver/stimulator implanted in the cochlea during a surgical procedure. The processor analyzes incoming sounds picked up by a microphone, converts them into electrical signals, and sends them to the transmitter coil. The transmitter is coupled to the implanted receiver coil, allowing the signals to be wirelessly transmitted through the skin. These electrical pulses then travel to the electrode array inside the cochlea, stimulating the cochlear nerve, to create the perception of sound.

The cochlea is a small, intricate, helical structure consisting of three fluid-filled channels separated by thin membranes. The electrode array of the implant is typically placed into the channel known as the scala tympani. An optimal configuration consists of placing the electrode array such that each electrode pad is in contact with the neural endings it stimulates, i.e., coiled along the modiolus with the electrode pads pointing inward toward the dense network of spiral ganglion neurons.

Due to the spiral shape of the channels, the electrode array becomes continually more difficult to insert as the frictional forces increase. This leads to two potential problems for cochlear implants: intracochlear trauma and/or incomplete insertion.

Intracochlear trauma refers to the damage caused by the electrode array scraping or pushing on the sensitive anatomy inside the cochlea. The most common cause of such trauma is the inter-scalar partition separating the scala tympani and the scala vestubuli. The inter-scalar partition consists of the osseous spiral lamina, Reissner's membrane, and the basilar membrane. The basilar membrane serves the vital function of transforming incoming sounds waves into mechanical vibrations that move the hair cells, causing them to create the electrical impulses sent to the auditory nerve. Experiments have shown that forces as low as 42 mN, very near the minimal force perceptible by humans, can rupture the inter-scalar partition. This means that despite the utmost care by experienced surgeons, translocation of the electrode array occurs in 25-33% of cases, resulting in the loss of any residual hearing.

Incomplete insertions occur for the same reason: the friction builds up until it reaches a point where the electrode array cannot overcome it without buckling. Even if trauma is avoided, speech outcomes are still negatively impacted. First, incomplete insertions can leave one or more electrodes outside the cochlea. In the best case, these are deactivated by the audiologist, reducing the number of usable channels. However, the incidence of extracochlear electrodes is underreported. The second problem is that incomplete insertions reduce the accessible frequency range. Nerves near the basal end of the cochlea are responsible for the perception of high frequency tones, while lower frequency waves propagate deeper before stimulating nerves more apical. These lower frequencies are particularly important for discerning speech.

One problem with such implants is that surgeons currently receive no feedback on whether the implant is correctly placed in the cochlea. Poor positioning may result in the electrodes not being positioned properly. For example, if the electrodes are not inserted deeply enough, the cochlear implant cannot provide high-quality hearing. Another problem is if the electrodes are placed far from the nerves. This may result in crosstalk between electrodes and thus requires large power consumption by the implant to stimulate the nerves. Currently, surgeons have no way of knowing if the electrode array of the implant is positioned properly in the cochlea. Feedback currently only occurs after the patient has been closed up and the implant is activated.

Thus, there is a need for a method to determine the proximity between an electrode array of a cochlear implant and biological tissues of the channel of the cochlea. There is also a need for a system that ensures real-time feedback that a cochlear implant is properly deployed when inserted in a patient. There is a further need for accurate feedback position signals during automatic insertion of a cochlear implant. There is also a need for a system to determine the final electrode positions on the implant to enhance programming of the cochlear system after implantation.

SUMMARY

In one example, a location system for an implant is disclosed. An implant has an electrode array including a first electrode and a second electrode. The electrode array is insertable into an electrically conductive volume relative to a structure of interest in a patient. The system includes a pulse generator generating a current pulse on the first and second electrodes. A controller is coupled to the first and second electrodes and the pulse generator. The controller measures the differential voltage across the pair of electrodes during the current pulse. The controller determines the proximity between the structure of interest and the segment of the electrode array between the first and second electrodes based on the differential voltage between the first and second electrodes.

Another disclosed example is a method to determine the location of an implant relative to a structure of interest. The implant has an electrode array including a first electrode and a second electrode. The electrode array is inserted in proximity of the structure of interest in an electrically conductive volume. A biphasic current pulse is applied between the first electrode and the second electrode. The differential voltage between the first electrode and the second electrode is measured while the current pulse is applied. The proximity between the tissue wall and the segment of the electrode array between the first and second electrodes is determined based on the differential voltage between the first and second electrodes.

The above summary is not intended to represent each embodiment or every aspect of the present disclosure.

Rather, the foregoing summary merely provides an example of some of the novel aspects and features set forth herein. The above features and advantages, and other features and advantages of the present disclosure will be readily apparent from the following detailed description of representative embodiments and modes for carrying out the present invention when taken in connection with the accompanying drawings and the appended claims.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

The disclosed system and method are directed toward location of an implant such as a cochlear implant during the implantation procedure, to allow correct placement of the implant in relation to a biological structure of interest in an electrically conductive volume area. One example of a biological structure of interest may be a tissue wall, such as an interior scala tympani channel in the cochlea. The volume of the interior scala tympani channel is filled with an electrically conductive perilymph fluid. A current pulse is applied to two electrodes of the array of electrodes of the cochlea implant. The voltage difference measured from the electrodes is associated with the volume of fluid between the electrodes and the inner wall of the interior scala tympani channel of the cochlea and therefore the proximity of the electrodes to the inner wall. The determined proximity may be used to correct the location of the electrode array to avoid intracochlear trauma. The location data may also be used to avoid incomplete insertion of the electrode array in the cochlea.

Figure 1A:
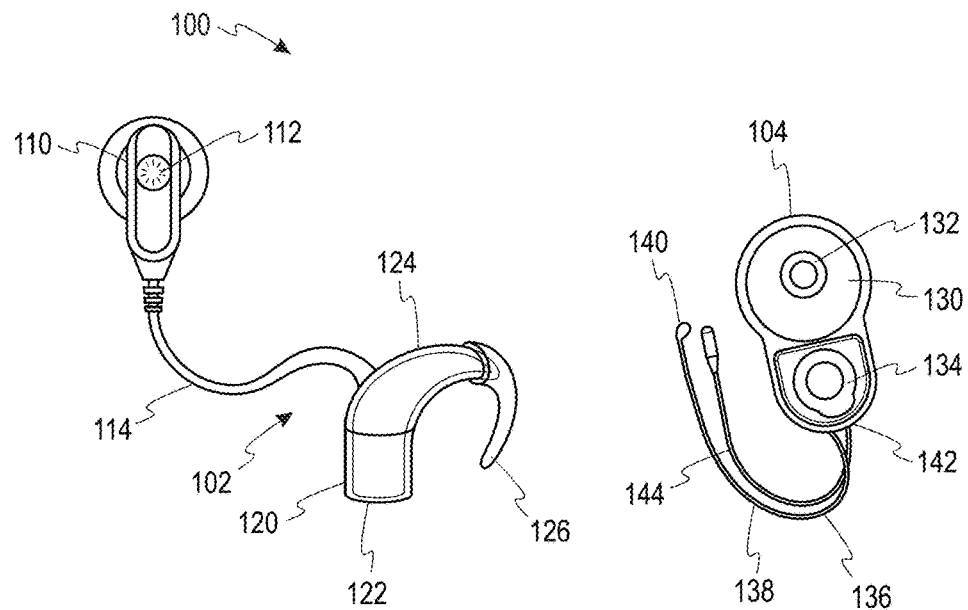
FIG. 1A is a view of internal and external components of a cochlear implant system according to one embodiment.

FIG. 1A shows the components of a cochlear implant system 100 in one embodiment that may be used to determine the location of an electrode array of an implant in the cochlea. The cochlear implant system 100 includes an external component 102 and an internal implant 104. The external component 102 and external implant 104 are shown separate from an ear 106 of the patient in FIG. 1A. Elements of the external component 102 and the internal implant 104 are also shown inserted in the ear 106 of a patient in FIG. 1B. The internal implant 104 is inserted into the head of the patient near the ear 106 in a surgical procedure. As will be explained, a location system may be electrically coupled to the internal implant 104 during the implantation procedure to properly position the internal implant 104. In this example, the location system may transmit and receive wireless signals to the internal implant 104 during the implantation procedure. Alternatively, wires and a suitable mating connector may be used to transmit and receive signals to the internal implant 104 from the location system, and the wires and connector may be removed when the internal implant 104 is properly implanted in the patient.

The external component 102 includes a transmitter 110, an external magnet 112 and a cable 114. The cable 114 connects the transmitter 110 to an electronics module 120. The electronics module 120 includes a speech processor module 122 and a microphone 124. The electronics module 120 includes a hook 126 that allows the electronics module 120 to be attached to the ear 106. The transmitter 110 is attached to the area of the head just above the ear 106 by the magnet 112 being attracted to a corresponding magnet on the internal implant 104. The speech processor module 122 includes a digital signal processor (DSP), a battery, and other electronics. Sounds that are picked up by the microphone 124 are processed by the DSP and converted to signals that are sent to the transmitter 110 through the cable 114. The transmitter 110 includes a coil that transmits the processed signals to the internal implant 104 through the skin of the patient's head.

Figure 1B:
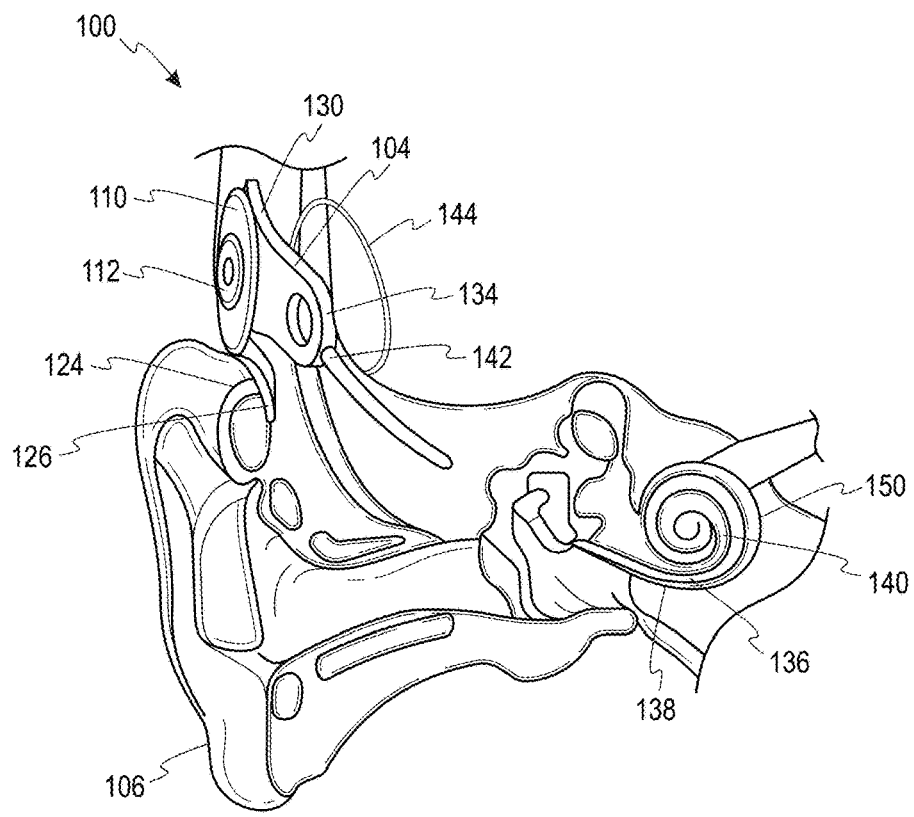
FIG. 1B is a cutaway view of the cochlear implant system in FIG. 1A inserted in an ear.

The internal implant 104 includes a receiving antenna 130, an internal magnet 132, a receiver 134 and an electrode array 136 with exterior electrodes 138. The electrode array 136 includes a distal tip 140 and a proximal plug end 142 that is attached to the receiver 134. An optional ground lead 144 may be inserted in a muscle near the ear 106. The electrode array 136 is flexible and may be coiled to be inserted into the channels of a cochlea 150 (FIG. 1B) of the ear 106. The electrode array 136 includes the electrodes 138 that are periodically spaced apart along the exterior of the electrode array 136. Signals from the receiver 134 representing the received sound from the microphone 124 are transmitted to the electrodes 138 of the electrode array 136. The electrodes 138 may stimulate the nerves lining the interior walls of the channel of the cochlea 150 and thus recreate the received sound. As shown in FIG. 1B, the internal implant 104 is implanted over the ear 106 where the receiving antenna 130 may be in proximity with the transmitter 110. The transmitter 110 is fixed in proximity to the receiving antenna 130 by the external magnet 112 being attracted to the internal magnet 132.

Figure 2A:
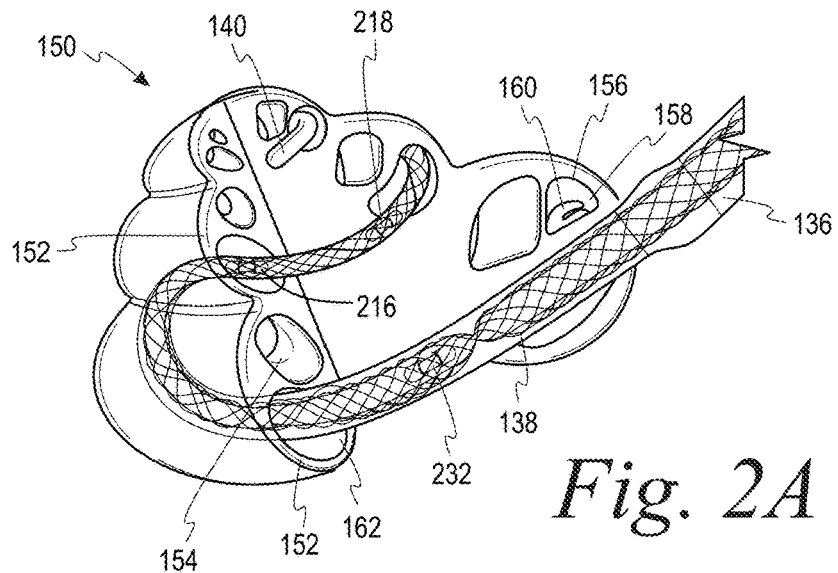
FIG. 2A is a perspective view of the cochlear implant of the system of FIG. 1A inserted in the cochlea according to one embodiment.
Figure 2B:
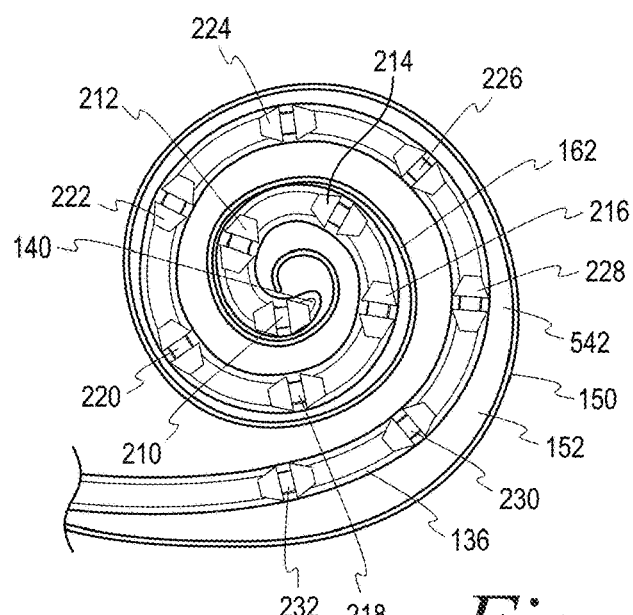
FIG. 2B is a cutaway view of the cochlear implant of the system of FIG. 1A inserted in the cochlea.

As shown in FIG. 1B, the ear 106 channels sound to a cochlea 150. FIGS. 2A and 2B are perspective and cutaway views of the electrode array 136 inserted in the cochlea 150. The cochlea 150 includes a scala tympani channel 152 and a scala vestubuli channel 154. An inter-scalar partition 156 separates the interior scala tympani channel 152 and the scala vestubuli channel 154. The inter-scalar partition 156 includes an osseous spiral lamina channel 158 and a basilar membrane 160. The interior volume of the scala tympani channel 152 is filled with perilymph fluid.

As shown in FIGS. 2A and 2B, the electrode array 136 is inserted in the scala tympani channel 152 of the cochlea 150. The cochlear nerve as well as the spiral ganglion is situated inside the cochlea 150. It is desirable for the electrodes 138 of the electrode array 136 to be placed in as close proximity as possible to an interior wall 162 of the interior scala tympani channel 152. As will be explained, the electrode array 136 may be connected to a location system to assist in the proper placement in the cochlea 150. Each of the electrodes 138 is connected to a wire that is encased by the electrode array 136. Each of the wires connected to the electrodes 138 is connected through the proximal plug end 142 to the receiver 134.

Figure 2C:
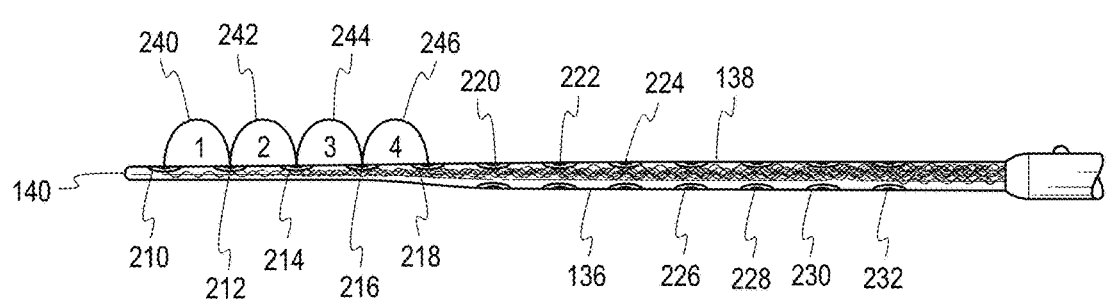
FIG. 2C is an enlarged view of the electrode array of the cochlear implant in FIG. 1A.

FIG. 2C is an enlarged view of the electrode array 136 prior to insertion in the cochlea 150. The electrodes 138 include a series of single electrodes 210, 212, 214, 216, and 218 near the tip 140. The electrode array 136 includes an additional set of seven electrode pairs 220, 222, 224, 226, 228, 230, and 232.

As will be explained, the location system provides current pulses to four channels defined by pairs of the electrodes 210, 212, 214, 216, and 218 for purposes of location determination of the electrode array 136 when inserted in the interior scala tympani channel 152. The voltage differentials for each of the channels are measured for determining the proximity between a segment of the electrode array 136 between the electrodes of the channel and to the inner wall of the interior scala tympani channel 152. Thus, in this example, a first channel 240 is defined by a voltage differential between the electrodes 210 and 212, a second channel 242 is defined by a voltage differential between the electrodes 212 and 214, a third channel 244 is defined by a voltage differential between the electrodes 214 and 216, and a fourth channel 246 is defined by a voltage differential between the electrodes 216 and 218.

The electrode array 136 in this example is a FLEX series electrode array manufactured by MED-EL of Innsbruck, Austria. Of course, any suitable electrode array of an implant may employ the principles disclosed herein. In this example, the electrode array 136 includes 12 electrodes 138, but it is contemplated that more or less electrodes may be used.

Figure 3:
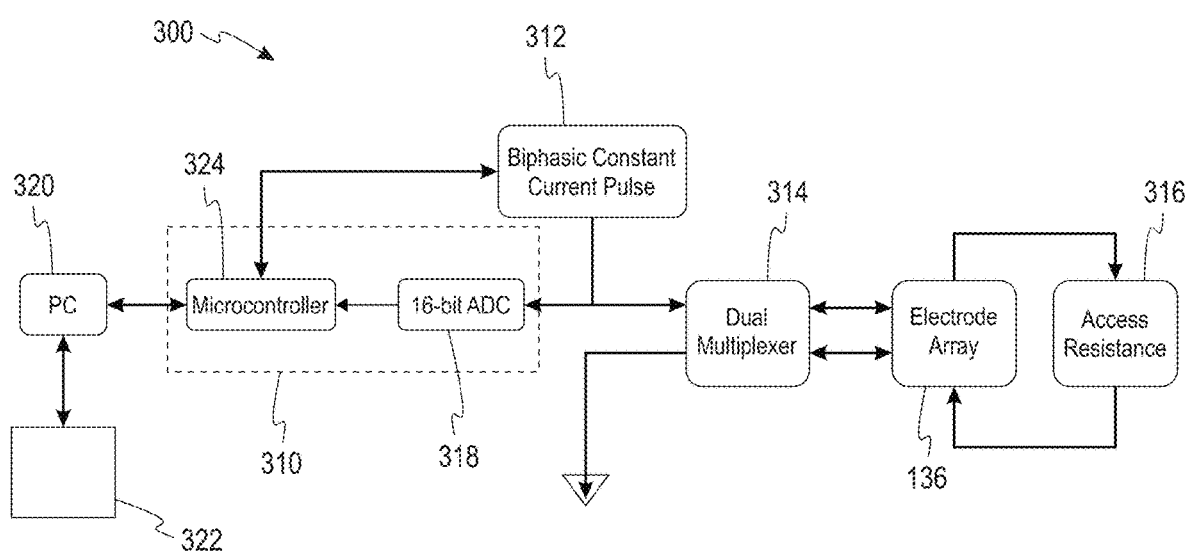
FIG. 3 is an example multi-channel implant location system that determines the location of a cochlear implant within an ear during the implant procedure.

FIG. 3 is a block diagram of a location system 300 for determining the location of the electrode array 136 in the exterior of the interior scala tympani channel 152 by the electrodes 138 as shown in FIGS. 2A-2B. The location system 300 includes a microcontroller unit 310. In this example, the microcontroller unit 310 may be the microcontroller on the Teensy 3.2 development kit manufactured by PJRC.COM, LLC, but any suitable processing device such as a microcontroller, processor, application specific integrated circuit (ASIC), programmable logic device (PLD), field programmable logic device (FPLD), field programmable gate array (FPGA), discrete logic, or the like may be used. The microcontroller unit 310 is coupled to a pulse generation circuit 312. The pulse generation circuit 312 includes a single output that generates bi-phasic constant current pulses at a predetermined frequency controlled by the microcontroller unit 310 in this example. The pulses are input to a multiplexer 314 that directs the pulse signal to different channels selected by the microcontroller unit 310. The current pulse inputs are selected by the multiplexer 314 to be applied to different electrode pairs of the electrode array 136 corresponding to different channels. The electrodes of the electrode array 136 are in proximity to the inner wall of the interior scala tympani channel 152 in FIGS. 2A-2B. The perilymph fluid filling this distance is represented by an access resistance 316. The voltage difference between the selected electrodes is fed back from the multiplexer 314 to an analog to digital (A/D) converter 318. In this example, the A/D converter 318 is integrated into the microcontroller unit 310. The output of the A/D converter 318 is input to an internal processing unit 324 of the microcontroller unit 310.

In this example, the microcontroller 310 causes a bi-phasic current pulse to be applied by the pulse generation circuit 312 and collects output voltage signals over the duration of the positive phase of the bi-phasic pulse. The microcontroller 310 determines the voltage difference between the selected electrodes during the positive phase of the pulse. The microcontroller 310 in this example executes a routine to cycle through four different channels of electrode pairs such as the channels 240, 242, 244, and 246 in FIG. 2C. The collected voltage differential data is converted to impedance data and is sent to a computer 320 that analyzes the collected impedance data to determine the position of the electrode array 136 relative to the inner wall of the interior scala tympani channel 152 of the cochlea 150. An artificial intelligence module 322 may be used as part of this analysis. The resulting real-time location of the implant may be used to assist a surgeon in maneuvering the electrode array 136 in the cochlea 150.

Figure 4:
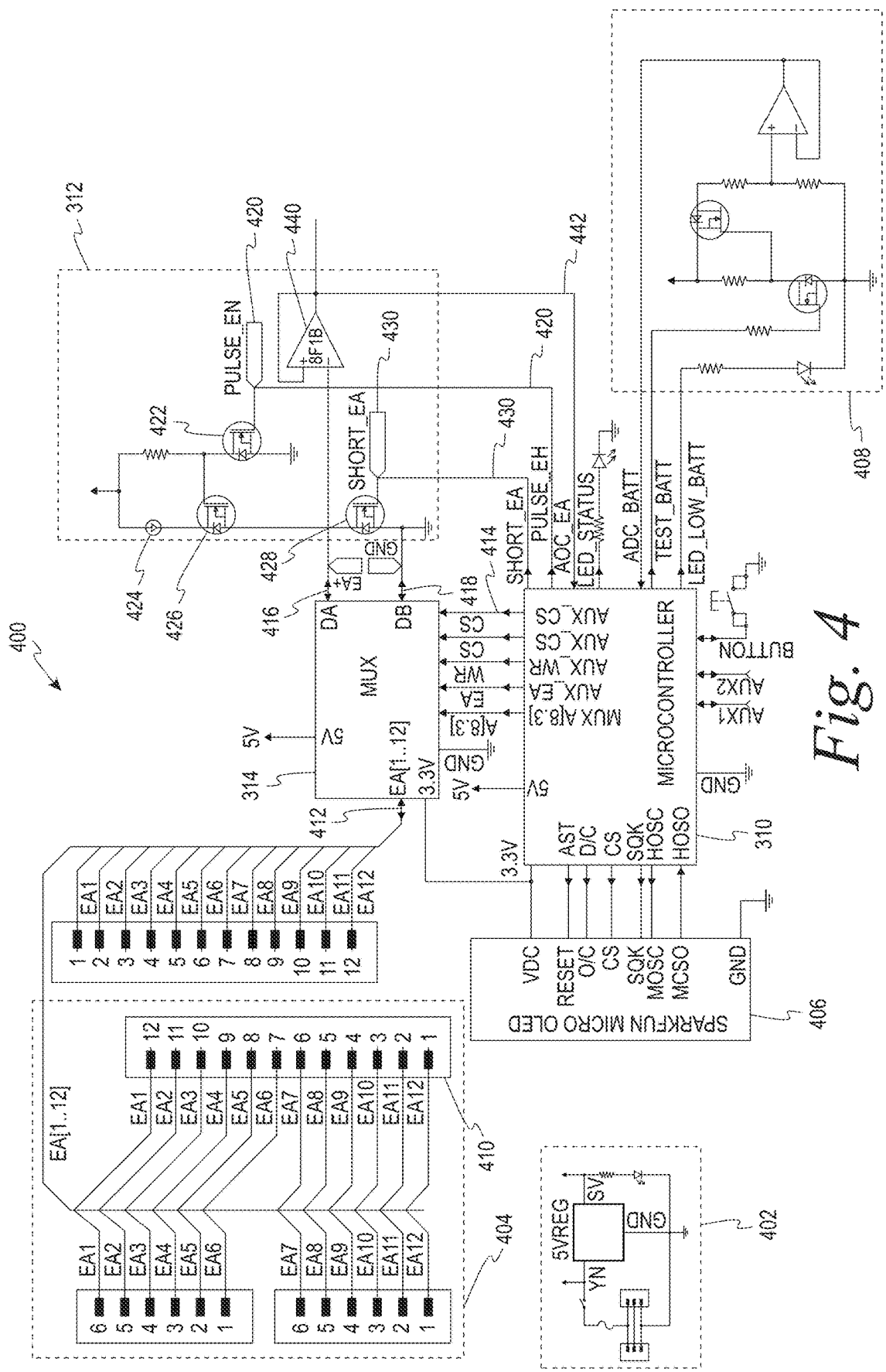
FIG. 4 is a circuit diagram of the components of the implant location system using multiple channels from the electrode array.

FIG. 4 is a block diagram of a multi-channel measurement system 400 that includes the microcontroller unit 310, the pulse generator 312, and the multiplexer 314 shown in FIG. 3. The system 400 includes a battery powered voltage regulator 402 that powers the microcontroller 310, the pulse generator 312, and the multiplexer 314. In this example, the system 400 is powered by battery rather than an external power source, such as through a USB connection, to provide a clean power source and reduce electrical noise. The system 400 includes an interface component 404 to provide the signal interface with the electrode array 136 during the positioning of the implant 104. An OLED circuit 406 is coupled to the microcontroller 310 to display indicators of operational status. A battery monitoring circuit 408 is coupled to the microcontroller 310 to ensure that adequate power is provided by the battery power source.

The interface component 404 includes a twelve-channel connector 410 that corresponds with the electrodes 138 of the electrode array 136. The input current signals and output voltage differential signals to and from the electrodes 138 on the electrode array 136 are wirelessly transmitted and received by the connector 410 to and from the receiver 130 of the internal implant 104 in FIGS. 1A-1B. The input and output signals from the connector 410 are connected to twelve bi-directional input/outputs 412 of the multiplexer 314. The selection inputs of the multiplexer 314 to select the specific ones of the input/outputs 412 are controlled by a series of control inputs 414 of the microcontroller 310. The multiplexer 314 also includes selectable input/output ports 416 and 418 that may be connected to the specific input/outputs 412. The input/output ports 416 and 418 are connected to receive the current pulse generated by the pulse generator 312 and output corresponding measured differential voltages of the electrodes 138 from the input/outputs 412.

In this example, the pulse generator circuit 312 generates the positive phase of the current pulse cycle by receiving an enable signal on an enable output 420 from the microcontroller 310. The enable signal from the output 420 is coupled to the gate of an N-type MOSFET 422. The source of the MOSFET 422 is coupled to ground and the drain is coupled to a resistor that is coupled to the voltage source (the battery). A constant current source 424 is coupled between the voltage source and the drain of a P-type MOSFET 426. The drain of the MOSFET 422 is also coupled to the gate of the MOSFET 426. The MOSFET 426 is coupled in series with another N-type MOSFET 428.

The pulse enable output 420 is connected to the gate of the MOSFET 422. The signal from the pulse enable output 420 pulls up the signal at the gate of the MOSFET 422. The enable signal thus turns on the MOSFET 422 and connects the constant current source 424 via the MOSFET 426 to provide a constant current of 100 μA in this example. A short enable output 430 of the microcontroller 310 is coupled to the gate of the MOSFET 428 that is coupled between the ports 416 and 418. When the pulse is enabled through the enable output 420, the short enable output 430 is pulled low to electrically short the two selected electrodes. It is only enabled after a pulse is complete to ensure that the voltage between the selected electrodes is zero before the next pulse starts. Otherwise, the voltages measured during the next pulse would be "biased" by any residual voltage, leading to inaccurate results. The current flows through the MOSFET 426 to the port 416 of the multiplexer 314, which is output on one of the input/outputs 412 to the corresponding electrode of the electrode array 136.

Thus, the MOSFET 426 connects the current from the current source 424 to an electrode such as the electrode 210 of the first channel 240 on the electrode array 136 in FIG. 2C that acts as the anode. The current flows through the perilymph fluid in the interior scala tympani channel 152 of the cochlea 150 in FIGS. 2A-2B to the other electrode 212 that is part of the first channel 240. The current then flows from the electrode 212 through the port 418 that is coupled to ground to complete the circuit.

The difference in voltages between the selected electrodes 210 and 212 in this example is a function of the variable access resistance 316 of the fluid in the distance to the channel wall. The differential voltage is measured through the output signal from the port 416. The port 416 is connected to the non-inverting input of an operational amplifier 440. The operational amplifier 440 is configured as a voltage follower to limit current leakage and serve as a signal buffer. The output of the operational amplifier 440 is connected to an analog to digital converter (ADC) input 442 on the microcontroller 310. During the positive current pulse generation, the microcontroller will sample the differential voltage from the ADC input 442 representing the differential voltage of the measured channel multiple times. As explained above, the electrodes 220, 222, 224, 226, 228, 230, and 232 in FIG. 2C are dual electrodes, with a contact on both the inner and outer walls of the interior scala tympani channel 152. These electrodes are not used in this example because as one side nears a wall of the interior scala tympani channel 152, ordinarily increasing Ra, the other side is moving away from the opposite wall, greatly reducing the desired effect.

The negative phase generation of the current pulse is triggered by the microcontroller 310 turning the MOSFET 422 off for a short amount of time. The microcontroller 310 then sends a control signal to the multiplexer 314 to reverse the electrodes that the ports 416 and 418 are connected to. Thus, in this example, the port 416 is connected to the electrode 212 while the port 418 is connected to the electrode 210. The microcontroller 310 then turns on the MOSFET 422, which causes a negative current pulse to be generated between the reversed electrodes 210 and 212 from the current source 424.

The microcontroller 310 may cycle through each channel of the electrode array 136 and repeat the process of generating a current pulse cycle and record voltage differential values during the positive phase of the cycle. In this example, the microcontroller 310 may cycle through the four channels 240, 242, 244, and 246 in FIG. 2C, but fewer or greater channels may be used. Further, channels may be defined by any of the electrodes on the electrode array 136. For example, a channel may be defined by the electrode 210 and the electrode 216 if desired.

In this example, the biphasic constant current pulse circuit 312 generates 100 μs duration current pulses at a constant current of 100 μA produced by the current source 424. In this example, the current source 424 provides constant current regulation and is a high-accuracy, microcurrent source such as a REF200 source manufactured by Texas Instruments. The multiplexer 314 regulates biphasic pulse generation and selection of each electrode pair. In this example, the multiplexer 314 is a dual 16-channel analog multiplexer (an ADG726 device manufactured by Analog Devices). It is to be understood that specialized circuits such as an ASIC or FPGA may be used to perform these functions. In this example, the firmware executed by the microcontroller 310 takes voltage measurements every 8.5 μs during the positive phase of the bi-phasic current pulse. To improve effective resolution, readings during 20 consecutive pulses for each channel in this example are recorded and individually averaged together As will be explained below, the microcontroller 310 runs a routine to fit a curve to these collected voltage values to estimate the true access resistance. Data from each of the channels allows the computer 320 to provide an estimate of the area defined by the segment between electrodes and the inner wall of the channel 152 in the cochlea 150. The calculated area is therefore proportional to the distance between the segment and the inner wall. The different channels therefore represent the respective distances to the inner wall of each of the segments of the electrode array 136 defined by the length between electrodes that define the channel as shown in FIG. 2C. The access resistance values determined by the microcontroller 310 are sent over a USB-serial connection to the computer 320 for further computing for determining the estimate of the area and real-time positioning such as by the machine learning module 322.

An alternate multi-channel system may use multiple pulse generators similar to the pulse generator 312 in FIG. 3 instead of the multiplexer 316. In such a system, each of the channels defined by the electrodes on the electrode array 136 is connected to the pulse output by one of the pulse generators. The differential voltages between electrodes may thus be measured simultaneously for each channel by the controller.

Figure 5:
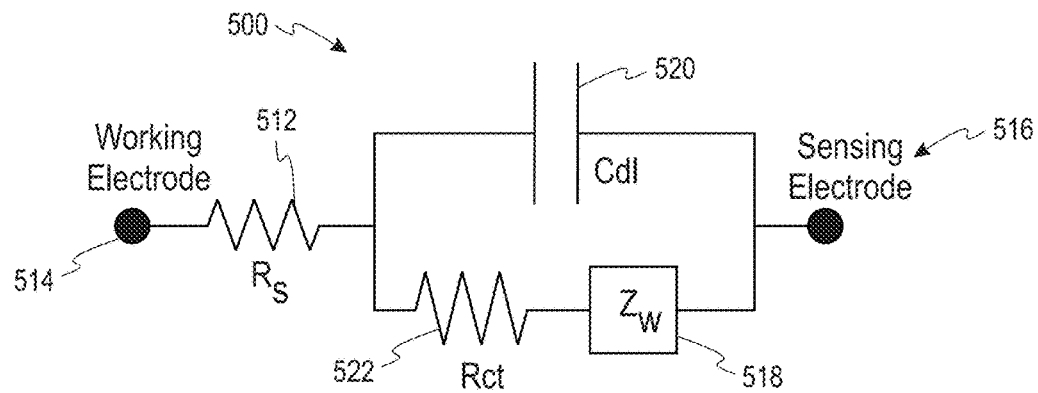
FIG. 5 is an equivalent electrical circuit model of the electrode-electrolyte interface according to the principles of the example system.

FIG. 5 shows an equivalent circuit 500 of a pair of electrodes of the electrode array 136 and the cochlea 150 in FIG. 1. The circuit 500 includes a resistor 512 that represents the access resistance of the perilymph fluid filling the channels of the cochlea 150. The pair of electrodes is represented by a working electrode 514 and a sensing electrode 516. Thus, for the first channel 240 in FIG. 2C, the working electrode 514 is the electrode 210 and the sensing electrode 516 is the electrode 212. For the second channel 242, the working electrode 514 is the electrode 212 and the sensing electrode 516 is the electrode 214.

The access resistance of the perilymph fluid-filled cochlea 150 best correlates with the proximity to the modiolus of the interior scala tympani channel 152 shown in FIG. 2A and the electrode pair of electrodes 514 and 516. Thus, this is the resistance of the perilymph fluid between the bipolar electrodes 514 and 516, which is correlated with the electrode-modiolar distance.

The other equivalent electrical elements in the circuit 500 are related to the physical properties of the electrode array 136, which remain mostly constant during the insertion of the electrode array 136. Thus, an impedance 518 is a Warbug impedance that models the ion diffusion process, a capacitor 520 represents the double layer capacitance, and a resistor 522 represents the charge transfer resistance. The capacitance represented by the capacitor 520 is created by the thin insulating space between the charged electrode surface and the nearby ions. The charge transfer resistance represented by the resistor 522 describes the electrical resistance experienced as electrons on the polarized electrode surface are transferred into charged ions in the electrolytic solution (perilymph in this case). Taken together, these terms model the total impedance of the electrode-electrolyte interface.

Figure 6:
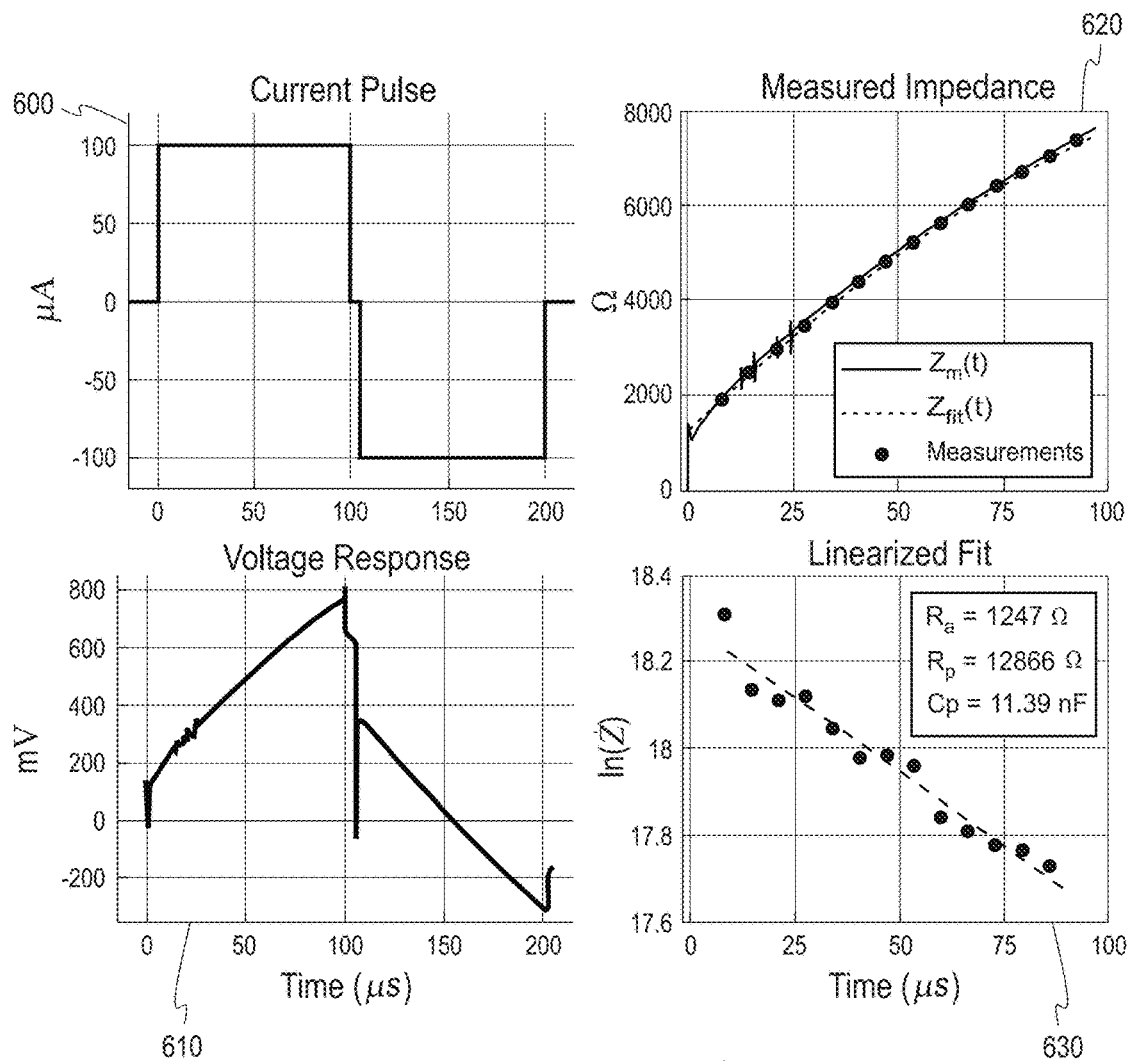
FIG. 6 is a series of graphs showing input and output signals and determined values from the location system in FIG. 3.

FIG. 6 is a set of graphs of different signals during the measurement process of the system 300. FIG. 6 shows a graph 600 that shows the current pulse signal generated by the pulse generator 312 and applied to two of the electrodes of the electrode array 136. As shown in the graph 600, the bi-phasic current pulse includes a cycle with a positive phase and a negative phase. A graph 610 shows the voltage response corresponding to the current pulse measured on a pair of electrodes. As shown, the voltage response increases during positive phase. A graph 620 shows the determined impedance from the voltage readings during the positive phase of the current pulse. A graph 630 shows the linearized fit of the measured voltages with the resistance and the capacitance of the electrode pad geometry.

Electrical impedance is the ratio of voltage to current in a circuit. Thus, an impedance measurement requires applying either a known voltage or current and measuring the response of the other. In the case of the example cochlear implants and the measurement system 300, a controlled current pulse is emitted and the voltage response is recorded during the pulse. A pulse with a significant DC component would create an ionic imbalance and alter the pH of the perilymph. Thus, the charge-balanced biphasic pulse is generated from the pulse generator 312 where the total amount of positive charge delivered in the positive current phase is balanced with an equal amount of negative charge in the negative current phase.

The example pulse generated by the pulse generator 312 is shown in the graph 600 in FIG. 6. At the high frequencies of the cochlear implant stimulation, the Warburg impedance is small. It can be neglected or assumed to be a part of the charge transfer resistance represented by the resistor 522 in FIG. 5. The measured voltage response from the application of the current signal in the graph 600 is shown in the graph 610 in FIG. 6. The voltage signal begins with a sharp rise due to the double layer capacitances initially behaving as short circuits. This means that the only impedance component seen at that first instance is the access resistance of the perilymph fluid. Thus, the access resistance may be determined by dividing the applied current by the voltage measured immediately after applying current.

Since the access resistance and the current are constants, the initial voltage is constant as well and simply biases any additional voltage created by other circuit elements. As the current continues until the end of positive phase, the charge across the capacitive components increases, causing the voltage to increase as well. This can be seen in the graph 610. The parallel resistance/capacitance causes the measured voltage to follow a standard first-order response, which can be modeled in order to solve for the parallel resistance and capacitance represented by the resistor 522 and the capacitor 520 in FIG. 5. The voltage measurements from the electrodes over the positive phase of the current pulse are converted into impedance values. A first-order response is fit by computing the least-squares solution of the linearized model as shown in the graph 630.

Since the parallel resistance and capacitance represented by the resistor 522 and the capacitor 520 in FIG. 5 are related to the exposed surface area of the electrode and electrode/electrolyte material properties, they can be assumed to remain constant for a given pair of electrodes. Such values are stored for the proximity determinations related to the channel. Thus, the calibration procedure need only be performed once for each channel.

Once the constant resistance and capacitance values are calibrated and stored for each channel, the proximity between the channel segment of the electrode array 136 defined by the electrodes such as electrodes 210 and 212 for the channel 240 in FIG. 2C and the inner wall of the interior scala tympani channel 152 of the cochlea 150 may be determined.

Figure 7:
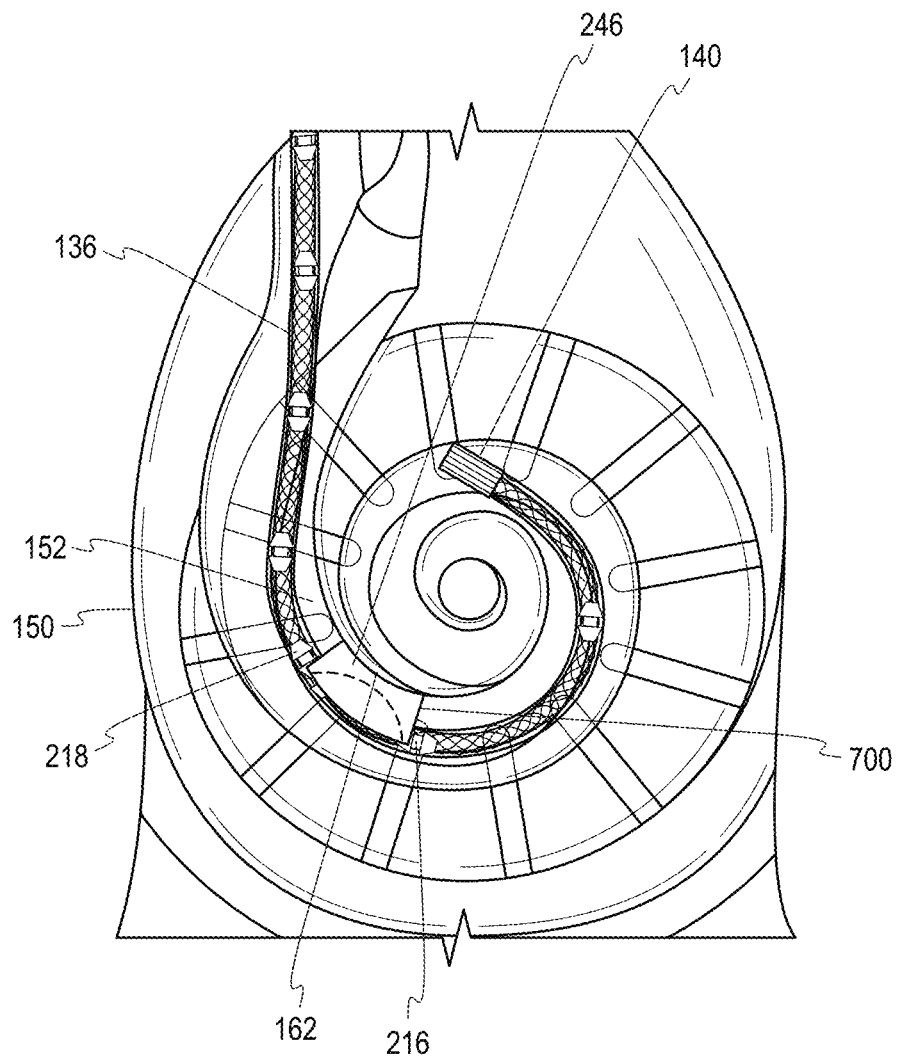
FIG. 7 is a cross section of the electrode array of a cochlear implant and the area determined by the location system in FIG. 3.

FIG. 7 shows a cross section of the implant array 136 in FIG. 2C inserted in the interior scala tympani channel 152 of the cochlea 150. An area 700 represents the area corresponding to the bipolar impedance between the electrodes 216 and 218. The key advantage of bipolar measurements is that biological influences on the current pulse are limited to this small area. In contrast, the current in a monopolar configuration must travel out of the cochlea 150 through the surrounding bone and tissue before reaching the sink electrode. The relationship between area 700 and bipolar impedance can be approximated by a power function:

$$R_a(A) = c_1 A^{c_2} + c_3$$

where Ra is the access resistance (resistance of the trapped volume of perilymph fluid), $c_1$, $c_2$ and $c_3$ are coefficients from model fitting of the constant resistance and capacitance in FIG. 5, and A is the area 700.

Since the access resistance, Ra, and the area, A, have an inverse relationship, the exponent $c_2$ must be negative. The constant, $c_3$, represents the horizontal asymptote of the function, which corresponds to the access resistance in an open channel as expressed by $$c3 = \lim_{A \to \infty} Ra(A)^n$$

The power function is then linearized by taking the natural logarithm of each side and rearranging:

$$\text{Ln}(Ra(A)-c_3) = c_2 \ln A + \ln c_1$$

The least squares linear regression of the linearized power function is then computed to determine the values of $c_1$ and $c_2$, where $y=\ln((Ra)A-c_3)$, $x=\ln(A)$, $c_1=b$ and $c_2=m$. After obtaining the coefficients, the power function may be rearranged in terms of the area, A, to obtain the model for estimating the area 700 as a function of the measured access resistance between the pair of electrodes:

$$A = \left(\frac{Ra - c3}{c1}\right)^{-C2}$$

The area of the trapezoid area 700 related to the proximity of the segment to the inner wall and may be classified by a machine learning routine.

Figure 8:
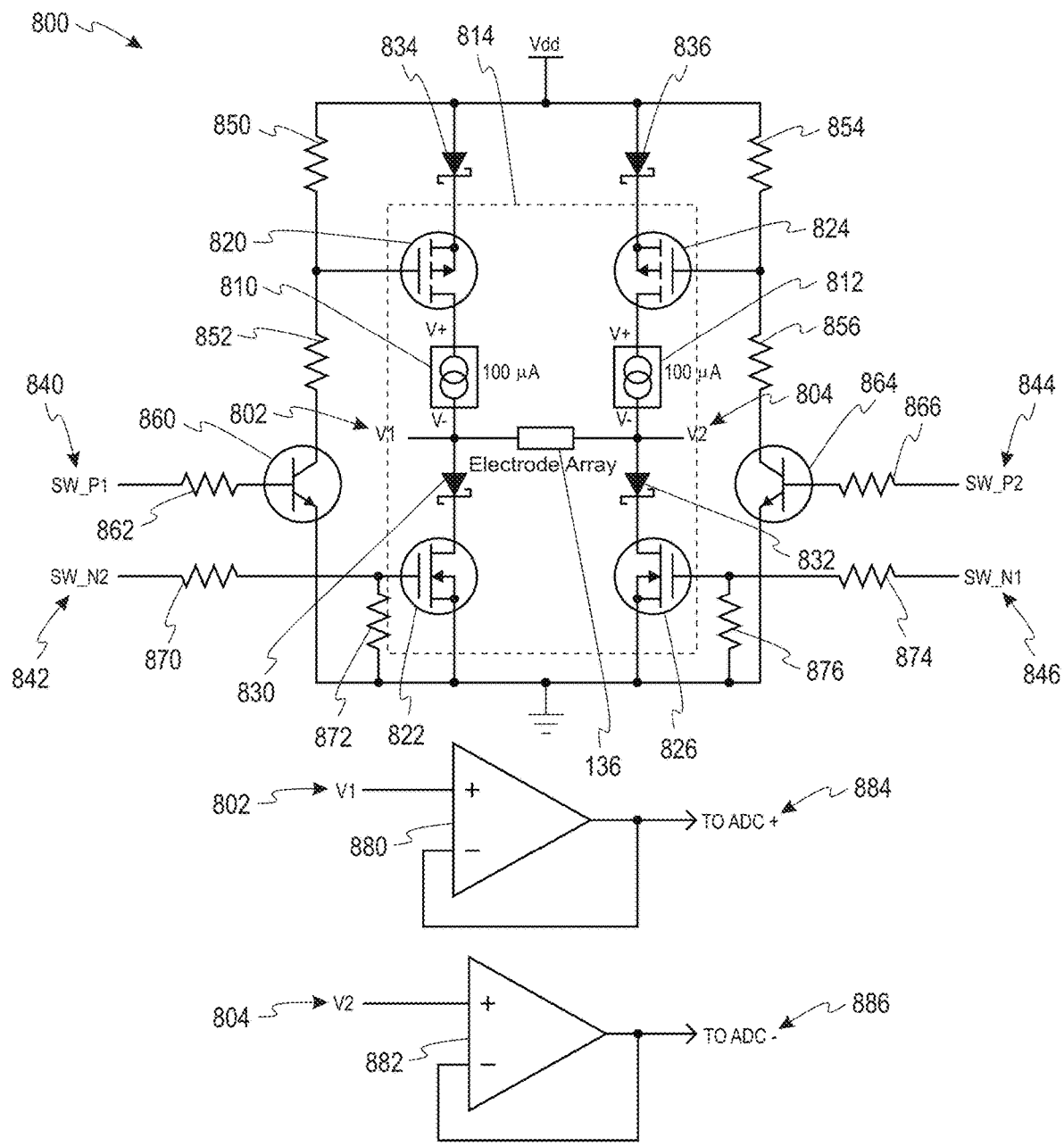
FIG. 8 is a circuit diagram of another example pulse generator for a location system for an electrode array of a cochlear implant.

FIG. 8 is a circuit diagram of an example single channel impedance measurement circuit 800 that may be incorporated with the location system 300 in FIG. 3. Unlike the multi-channel system 300 in FIGS. 3-4, the measurement circuit 800 determines the voltage differential from two electrodes 802 and 804. The differential voltage measurements during the application of a bi-phasic current pulse allows a microcontroller such as the microcontroller 310 in FIGS. 3-4 to determine the impedance and therefore the distance between the electrodes and a tissue wall such as the inner wall of the interior scala tympani channel 152 of the cochlea 150. In this example, the electrodes 802 and 804 are the electrodes 210 and 212 in FIG. 2C located closest to the tip 142 of the electrode array 136 in FIG. 2C for robotic insertion based on location data. In other applications, such as manual insertion, the electrodes 802 and 804 may be electrode pairs further from the tip 142 in FIG. 2C.

The measurement circuit 800 includes two current sources 810 and 812 that are alternatively connected to the electrodes 802 and 804 using a MOSFET based H-bridge 814 to create the bi-phasic pulse. The H-bridge 814 includes four MOSFETs 820, 822, 824, and 826. The positive lead of the current source 810 is coupled to the drain of the P-type MOSFET 820. The negative lead of the current source 810 is coupled to the electrode 802 of an electrode array such as the electrode array 136 and one end of a Schottky diode 830. The other end of the Schottky diode 830 is coupled to the drain of the N-type MOSFET 822.

Similarly, the positive lead of the other current source 812 is coupled to the drain of the P-type MOSFET 824. The negative lead of the current source 812 is coupled to the electrode 804 of the electrode array 136 and one end of a Schottky diode 832. The other end of the Schottky diode 832 is coupled to the drain of the N-type MOSFET 826. The drains of the MOSFETs 820 and 824 are tied to the voltage source via respective Schottky diodes 834 and 836.

In this example, four digital control outputs 840, 842, 844, and 846 of the microcontroller send control signals to the gates of the MOSFETs 820, 822, 824, and 826 respectively to control current flow through the electrode array through the electrodes 802 and 804. Thus, the microcontroller generates a positive cycle of the bi-phasic current pulse by turning on the MOSFETs 820 and 826 through the control outputs 840 and 846. The current source 810 thus is connected to complete a circuit between the voltage source and ground and thus generates current flow between the electrode 802 and the electrode 804 The microcontroller generates the negative cycle of the bi-phasic current pulse by turning off the MOSFETs 820 and 822 and turning on the MOSFETs 824 and 826 through the control outputs 844 and 846. The current source 812 thus is connected to complete a circuit between the voltage source and ground and thus generate current flow between the electrode 804 and the electrode 802.

Two resistors 850 and 852 form a voltage divider coupled to the gate of the MOSFET 820. The other end of the resistor 852 is coupled to the collector of a transistor 860. The output 840 is coupled through a resistor 862 to the base of the transistor 860. Correspondingly, two resistors 854 and 856 form a voltage divider to provide a voltage signal to the gate of the MOSFET 824. The other end of the resistor 854 is coupled to the collector of a transistor 864. The output 844 is coupled through a resistor 866 to the base of the transistor 864. The output 842 is connected to a resistor 870 and a resistor 872 to the gate of the MOSFET 822. The output 846 is connected to a resistor 874 and a resistor 876 to the gate of the MOSFET 826. Since the P-type MOSFETs 820 and 824 require higher voltage, the control signals are amplified by the respective transistors 860 and 864. The Schottky diodes 830 and 832 are used to control the source voltage below the voltage of the voltage source to allow the MOSFETs 820 and 824 to be fully turned off. The resistors 852 and 856 may be selected to change the rate that the MOSFETs 820 and 824 are turned off.

The electrode 802 is coupled to the non-inverting input of an operational amplifier 880 and the electrode 804 is coupled to the non-inverting input of another operational amplifier 882. The operational amplifiers 880 and 882 are arranged in a voltage follower configuration to buffer the output signals from the respective electrodes 802 and 804. The inverting inputs of the operational amplifiers 880 and 882 are connected in a feedback to the respective outputs. The outputs of the operational amplifiers 880 and 882 are coupled to inputs 884 and 886 of a built in analog to digital converter in the microcontroller such as the microcontroller 310 in FIG. 3. The output of the analog to digital converter is a digital value for the differential voltage across the electrodes 802 and 804 of the electrode array 136. The differential voltages are collected for each pulse cycle. The voltage values are processed to determine the distance of the electrode to the wall of cochlea as explained above.

The disclosed principles of the above described system may provide final placement position information as well as real-time feedback during the insertion of the electrode array 136. The OLED output 408 may be programmed to provide indicators as to the distance between the electrode array 136 and the inner wall of the interior scala tympani channel 152. This enables a surgeon to adjust the electrode positions immediately or withdraw the electrode array 136 and try again while performing the implantation procedure. For example, colors may indicate whether the distance is sufficient thus allowing a surgeon to adjust the positioning of the array 136 during the insertion procedure.

In order to achieve dependable real-time localization of the electrode array 136 during the insertion process, a more sophisticated model may be used to process the voltage signals gathered by the microcontroller 310. As a bipolar electrode pair moves towards or away from a tissue wall, the impedance values change smoothly. Thus, the history of the impedance measurements may be useful in addition to the current impedance value in determining proximity. There are many ways this type of heuristic could be implemented, but given the complexity of the modeled system, the machine learning module 322 is used. In this example, the machine learning module 322 is a Long Short-Term Memory (LSTM) recurrent neural network implemented using MATLAB's Deep Learning Toolbox.

In this example, the neural network is designed to take a sequence of values (e.g., impedances determined from the measured differential voltages from pulses applied during the period the insertion) as inputs and produce a selection of one of three classes corresponding to the proximity of the electrodes and thus the electrode array 136 and the inner wall of the interior scala tympani.

In this example, these proximity classes represent three possible location regions: a "modiolar" region (defined as less the 0.5 mm$^2$ between that channel's electrodes and the modiolar wall), a "lateral" region (defined as greater than 1:0 mm$^2$ between that channel's electrodes and the modiolar wall), and a "middle" region between the lateral and modiolar regions (defined as 0.5 mm$^2$ to 1.0 mm$^2$ between that channel's electrodes and the modiolar wall). Based on the training data, fewer or greater classification regions may be output by the machine learning module 322. In this example, the LSTM layer was given 120 hidden units and the network was trained using two of the three sets of trial data previously acquired. The third trial was then run through the network to evaluate its accuracy. The overall accuracy was over 93%. The modiolar region was classified successfully 87.6% of the time, the middle region was classified successfully 87.9% of the time and the lateral region was classified 96.1% of the time. The trained network runs in real-time on the machine learning module 322 as new measurements are streamed in from the microcontroller 310.

The output may be displayed in any number of ways to provide a surgeon real time feedback as to the location of a segment or segments of the implant electrode 136. For example, the feedback may include colors to indicate the regions, or a graphical display with an image of the cochlea and the position of the implant array 136 rendered based on the output of the machine learning module 322 as to the location of the various segments.

Figure 9:
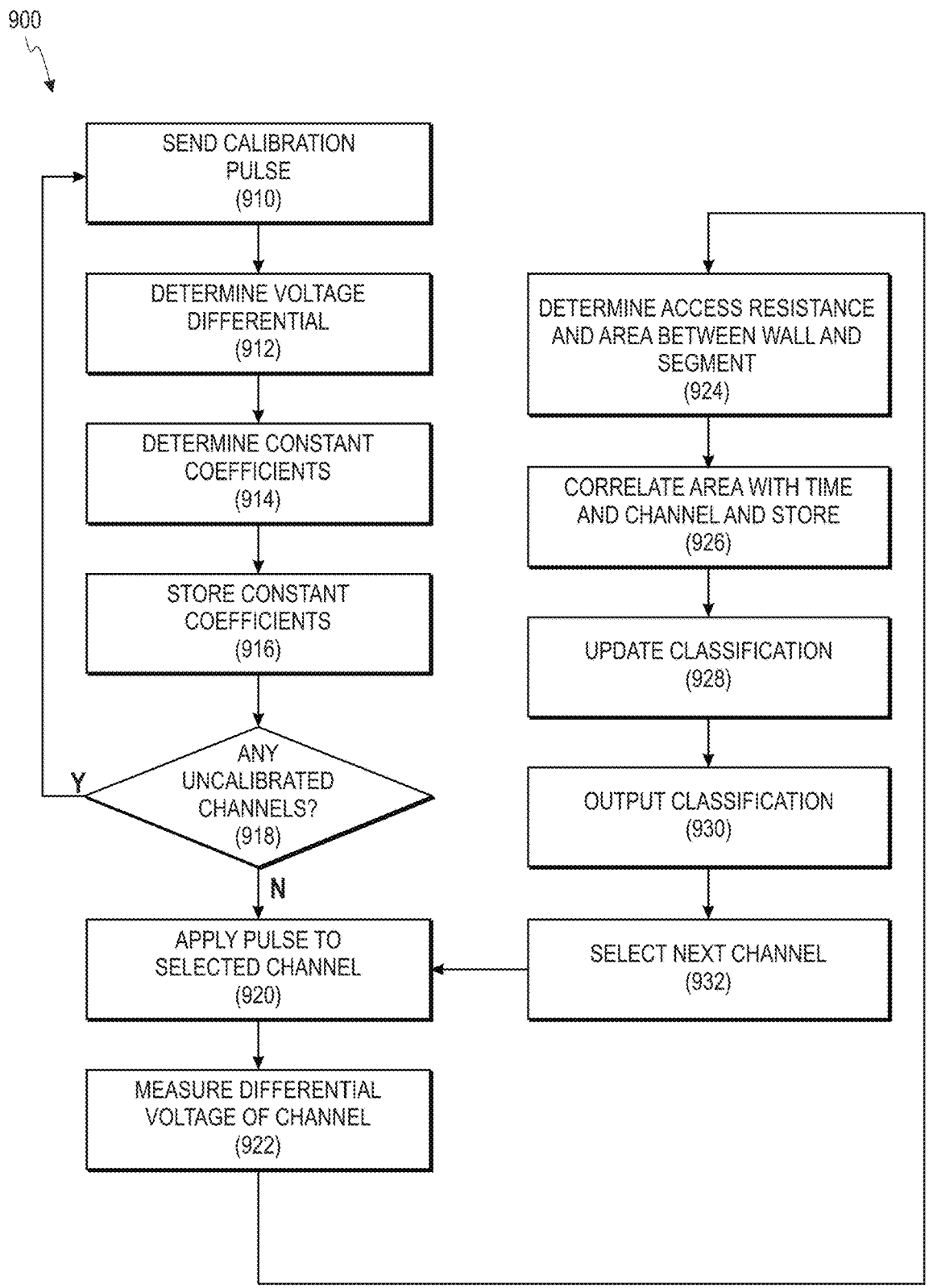
FIG. 9 is a flow diagram of the process of determining the location of an implant such as a cochlear implant during implantation.

FIG. 9 is an example machine readable instruction for the system 300 for determining the proximity of the electrodes of an electrode array to a tissue wall. In this example, the machine readable instructions comprise an algorithm for execution by: (a) a processor; (b) a controller; and/or (c) one or more other suitable processing device(s). The algorithm may be embodied in software stored on tangible media such as flash memory, CD-ROM, floppy disk, hard drive, digital video (versatile) disk (DVD), or other memory devices. However, persons of ordinary skill in the art will readily appreciate that the entire algorithm and/or parts thereof can alternatively be executed by a device other than a processor and/or embodied in firmware or dedicated hardware in a well-known manner (e.g., it may be implemented by an application specific integrated circuit [ASIC], a programmable logic device [PLD], a field programmable logic device [FPLD], a field programmable gate array [FPGA], discrete logic, etc.). For example, any or all of the components of the interfaces can be implemented by software, hardware, and/or firmware. Also, some or all of the machine readable instructions represented by the flowcharts may be implemented manually. Further, although the example algorithm is described with reference to the flowchart illustrated in FIG. 9, persons of ordinary skill in the art will readily appreciate that many other methods of implementing the example machine readable instructions may alternatively be used. For example, the order of execution of the blocks may be changed, and/or some of the blocks described may be changed, eliminated, or combined.

The flow diagram 900 in FIG. 9 initiates the location determination by triggering an initial calibration bi-phasic current pulse through a first channel defined by two electrodes on the electrode array 136 in FIG. 2C (910). The microcontroller samples the voltage output between the electrodes of the channel (912). The microcontroller then determines the constant coefficients by fitting the voltage readings to the expected response of the equivalent circuit model (914). The determined constant coefficients for the channel are then stored in memory (916). The routine then determines whether there are any other channels remaining (918). If further channels exist, the routine loops back to sending a calibration pulse (910) and obtaining the constant coefficients.

After all of the constant coefficients are determined and thus no further channels remain (918), the routine then starts with the first channel and applies a bi-phasic current pulse to the electrodes of the channel (920). The routine then measures the differential voltage from the electrodes of the channel (922). The routine then calculates the impedance to determine the access resistance and uses the power function and stored constant coefficients to determine the area between the segment defined by the electrodes of the channel and the wall of the cochlea (924). Alternatively, the machine learning module 322 can be used to determine the area between the segment defined by the electrodes of the channel and the wall of the cochlea. The determined area is correlated with the time and the channel and stored (926).

The routine then accesses the machine learning module 322 to update the classification of the real-time location of the segment of the channel based on the past data and the input of the determined area (928). The routine then outputs the proximity classification ("modiolar" region, "lateral" region, or "middle" region) for the segment of the electrode array 136 relating to the selected channel (930). The routine then selects the next channel (932) and applies the bi-phasic current pulse to the electrodes of the next selected channel (920).

The location system 300 may be used to determine the final position of the electrode array 136 relative to the cochlear 150. Another application for the above described concepts may be an example automated surgery system that may use the location system described herein to guide the insertion of the implant. The location system and method may also be applied for other types of implants such as those used for spinal cord stimulation or deep brain stimulation. Further, although a current pulse is applied and a differential voltage is measured to determine proximity of the implant to the biological structure of interest, a voltage pulse may be applied to the electrodes and a current may be measured for determination of the proximity.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a," "an," and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilized to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A location system for an implant, comprising:
an implant having an electrode array including a first electrode and a second electrode, the electrode array insertable into an electrically conductive volume in proximity to a structure of interest in a patient;
a pulse generator including a constant current source and a switching transistor, wherein the pulse generator generates a current pulse on the first and second electrodes by controlling the switching transistor to apply the output of the constant current source for a predetermined duration;
a controller coupled to the first and second electrodes and the pulse generator, the controller operative to:
measure the differential voltage across the pair of electrodes during the current pulse; and
determine the proximity between the structure of interest and a segment of the electrode array between the first and second electrodes based on the differential voltage between the first and second electrodes.

2. The location system of claim 1, wherein the implant is a cochlear implant insertable into a scala tympani of a cochlea, and wherein the proximity is determined relative to an inner wall of the scala tympani of the cochlea.

3. The location system of claim 2, wherein the first electrode is located in proximity to a tip of the electrode array, wherein the tip is inserted first into the cochlea.

4. The location system of claim 1, wherein the electrode array includes a third electrode.

5. The location system of claim 4, further comprising a multiplexer having a control input coupled to the controller and an input coupled to the pulse generator, and selectable input/outputs coupled to the electrodes, wherein the controller is operable to:
control the multiplexer to switch the inputs from the pulse generator from the first and second electrodes to the second and third electrodes;
cause the generation of a current pulse from the pulse generator to the second and third electrodes;
measure the differential voltage across the second and third electrodes during the current pulse; and
determine the proximity between the structure of interest and a segment of the electrode array between the second and third electrodes based on the differential voltage between the second and third electrodes.

6. The location system of claim 4, further comprising a second pulse generator having a control input coupled to the controller and outputs coupled to the second and third electrodes, wherein the controller is operable to:
cause the generation of a current pulse from the second pulse generator to the second and third electrodes;
measure the differential voltage across the second and third electrodes during the current pulse; and
determine the proximity between the structure of interest and a segment of the electrode array between the second and third electrodes based on the differential voltage between the second and third electrodes.

7. The location system of claim 1, wherein the current pulse is a bi-phasic pulse including a positive phase and a negative phase, and wherein the differential voltage is measured during the positive phase.

8. The location system of claim 1, further comprising a machine learning module coupled to the controller, wherein the machine learning module is operable to:

collect differential voltage data over a period of time;
learn to classify the proximity of the first and second electrode based on the collected differential voltage data; and
output a classified proximity of the electrode array relative to the structure of interest based on the differential voltage.

9. The location system of claim 1, wherein the controller is further operative to:
calibrate constant values related to the first two electrodes based on determining an initial access resistance from a differential voltage measured between the first and second electrodes at a constant current; and
store the calibrated constant values; and wherein the proximity is determined based on the calibrated constant values.

10. A method to determine the location of an implant relative to a structure of interest, the implant having an electrode array including a first electrode and a second electrode, the method comprising:
inserting the electrode array in an electrically-conductive volume in proximity of the structure of interest;
applying a current pulse generated by a pulse generator between the first electrode and the second electrode wherein the pulse generator generates the current pulse by controlling a switching transistor to apply the output of a constant current source for a predetermined duration;
measuring the differential voltage between the first electrode and the second electrode while the current pulse is applied; and
determining the proximity between the structure of interest to a segment of the electrode array between the first and second electrodes based on the differential voltage between the first and second electrodes.

11. The method of claim 10, wherein the implant is cochlear implant insertable into a scala tympani of a cochlea, and wherein the proximity is determined relative to an inner wall of the scala tympani of the cochlea.

12. The method of claim 11, wherein the first electrode is located in proximity to a tip of the electrode array, wherein the tip is inserted first into the cochlea.

13. The method of claim 10, wherein the electrode array includes a third electrode.

14. The method of claim 11, further comprising:
controlling a multiplexer to switch the pulse generator from the first and second electrodes to the second and third electrodes;
applying a current pulse to the second and third electrodes;
measuring the differential voltage across the second and third electrodes during the current pulse; and
determining the proximity between the structure of interest and a segment of the electrode array between the second and third electrodes based on the differential voltage between the second and third electrodes.

15. The method of claim 11, further comprising:
applying a current pulse generated by a second pulse generator to the second and third electrodes;
measuring the differential voltage across the second and third electrodes during the current pulse; and
determining the proximity between the structure of interest and a segment of the electrode array between the second and third electrodes based on the differential voltage between the second and third electrodes.

16. The method of claim 10, wherein the pulse generator generates a bi-phasic pulse.

17. The method of claim 16, wherein the bi-phasic current pulse includes a positive phase and a negative phase, and wherein the differential voltage is measured during the positive phase.

18. The method of claim 10, further comprising:
collecting differential voltage data over a period of time;
training a machine learning module to classify the proximity of the first and second electrode based on the collected differential voltage data; and
via the machine learning module, output a classified proximity of the electrode array relative to the structure of interest based on the differential voltage.

19. The method of claim 10, further comprising:
calibrating constant values related to the first two electrodes based on determining an initial access resistance from a differential voltage measured between the first and second electrodes at a constant current; and
storing the calibrated constant values; and wherein the proximity is determined based on the calibrated constant values.

20. A location system for an implant, comprising:
an implant having an electrode array including a first electrode and a second electrode, the electrode array insertable into an electrically conductive volume in proximity to a structure of interest in a patient;
a pulse generator generating a current pulse on the first and second electrodes, wherein the current pulse is a bi-phasic pulse including a positive phase and a negative phase;
a controller coupled to the first and second electrodes and the pulse generator, the controller operative to:
measure the differential voltage across the pair of electrodes during the positive phase of the current pulse; and
determine the proximity between the structure of interest and a segment of the electrode array between the first and second electrodes based on the differential voltage between the first and second electrodes.

* * * * *